United States Patent [19]  
Driscoll et al.

[11] Patent Number: 4,549,953
[45] Date of Patent: Oct. 29, 1985

[54] ION-SELECTIVE ELECTRODES

[75] Inventors: John N. Driscoll, Wellesley Hills; Edwards S. Atwood, Natick, both of Mass.

[73] Assignee: HNU Systems, Inc., Newton, Mass.

[21] Appl. No.: 644,772

[22] Filed: Aug. 27, 1984

Related U.S. Application Data

[63] Continuation-in-part of Ser. No. 496,113, May 19, 1983, abandoned.

[51] Int. Cl.$^4$ .............. G01N 27/30; C01B 19/00; C01B 17/00
[52] U.S. Cl. .................. 204/419; 423/508; 423/511
[58] Field of Search ............ 204/419; 423/508, 511, 423/42, 48

[56] References Cited

U.S. PATENT DOCUMENTS

| | | | |
|---|---|---|---|
| 3,563,874 | 2/1971 | Ross et al. | 204/195 |
| 3,696,038 | 10/1972 | Davies et al. | 423/511 X |
| 3,806,438 | 4/1974 | Higashiyama et al. | 204/419 |
| 3,809,636 | 5/1974 | Higashiyama et al. | 204/195 |
| 4,071,427 | 1/1978 | Cheng et al. | 204/195 |
| 4,172,778 | 10/1979 | van de Leest et al. | 204/195 |
| 4,396,486 | 8/1983 | Mruk et al. | 204/419 |

Primary Examiner—G. L. Kaplan

[57] ABSTRACT

Electrochemical cell including an ion-specific membrane containing, in one aspect, Ag, S, and Sb and in another aspect a ternary compound of Ag, S and one of As, Sb, Se and Te. Methods are disclosed for making ternary compounds of Ag, S and one of Se, Sb, Te and As.

10 Claims, 2 Drawing Figures

ION-SELECTIVE ELECTRODES

BACKGROUND OF THE INVENTION

This application is a continuation-in-part of U.S. Application Ser. No. 496,113, filed May 19, 1983 and now abandoned.

This invention relates to electrochemical analysis and more particularly to ion-specific electrochemical cells.

Such cells are known in which the ion-specific element is a silver-containing impervious membrane separating a reference and a sample solution containing an unknown amount of an ion to be measured, e.g. halide, arsenite, cyanide, or sulfide. Cheng et al. U.S. Pat. No. 4,071,427 describes an arsenite sensing cell employing a membrane containing a mixture of $Ag_2S$ and $Ag_3AsO_3$. Ross et al. U.S. Pat. No. 3,563,874 describes a halide sensing cell employing a membrane containing a mixture of silver sulfide and silver halide. Van de Leest et al. U.S. Pat. No. 4,172,778 describes a halide sensing cell employing a membrance containing a mixture of $Ag_3SBr$ and $Ag_3SI$. Mruk et al. U.S. Pat. No. 4,396,486 describes an ion selective electrode membrane made by pressing at 350° F., a "coprecipitate of $Ag_2S$, $Ag_2Se$, CdS, and CdSe." The above patents are hereby incorporated by reference.

The present invention provides improved membranes for ion-specific electrochemical cells. Some of the membranes contain Ag, S, and either Sb or Te; preferably, these membranes contain a compound containing Ag and one of Sb or Te. Some of the membranes contain Ag, S, and one of Sb, Te, As, or Se, and are made by combining an aqueous solution of a silver salt with an aqueous solution of a compound containing S and one of Se, Sb, Te, or As to form a precipitate containing Ag, S, and one of Se, Sb, Te, or As, and subjecting the precipitate to elevated pressure at a temperature lower than 100° to form the membrane. The membranes are believed to contain a new class of ternary compounds of Ag, S, and one of Se, Sb, Te, or Ar.

In some preferred embodiments the ternary compound has the formula $Ag_3QS_3$, wherein Q is As or Sb.

In other preferred embodiments the ternary compound has the formula $Ag_4SZ$, wherein Z is Se or Te.

The membrane can also contain one of AgX, wherein X is a halogen; lead sulfide; cadmium sulfide; copper sulfide; mercury sulfide; silver cyanide; or silver thiocyanate. When such an additional component is present, the ternary silver compound makes up between 10 and 90 mole percent, more preferably 45 to 60 mole percent, and most preferably 50 mole percent, of the membrane.

The membranes of the invention are durable and provide the option of measuring any of the three elements of which they are composed. The membranes are also pressible under cold conditions (temperatures below 100° C.), and can be used as the pressible matrix for additional ion-specific materials which are desired to be employed but which do not press well themselves; examples of such materials are the silver halides, particularly silver iodide (for sensing iodide or cyanide); lead sulfide (for sensing lead); cadmium sulfide (for sensing cadmium); copper sulfide (for sensing copper); mercury sulfide (for sensing mercury); silver thiocyanate (for sensing thiocyanide); and silver cyanide (for sensing cyanide).

The membranes of the invention also provide the advantage of resistance to strong solvents such as iodide and cyanide. It is believed that this solvent resistance may be due to the Te, Sb, As, or Se, which might bind the silver more tightly within the membrane and thus protect it.

The membranes of the invention also have the advantage of providing close to Nernstian responses at low sample ion levels; this is perhaps a function of solvent resistance and the resultant small amount of silver which dissolves from the membrane and goes into solution.

Other objects, features, and advantages of this invention will be apparent to those skilled in the art from the following detailed description of preferred embodiments thereof, taken together with the accompanying drawings, in which.

Figure 1:
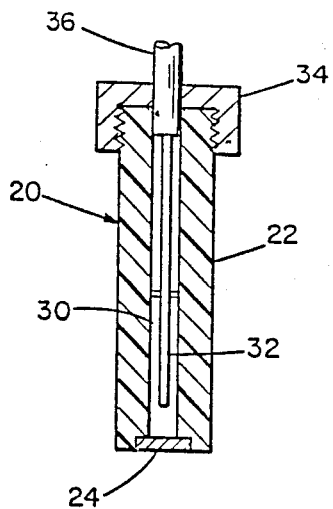
FIG. 1 is a diagrammatic side-elevation, in cross-section, of an electrochemical cell employing a membrane of the invention.

Certain of the components of the membranes of the invention occur naturally as minerals. Thioantimonite, believed to have the formula $Ag_3SbS_3$, occurs naturally as the mineral pyrargyrite, and the mineral prousite, believed to contain $Ag_3AsS_3$, and the mineral aguilarite, believed to contain $Ag_4SSe$, occur naturally. These minerals can be pressed to form membranes of the invention.

Alternatively, membrane materials containing Ag, S, and either Se or Te, and believed to contain a compound having the formula $Ag_4SZ$, can be made by dissolving solid sodium selenide or telluride (commercially available) in a 0.2M sodium sulfide solution and then combining the resulting solution with a dilute solution of silver ion (e.g. $AgNO_3$). The resulting precipitate is separated out, washed, and dried.

In more detail, the above procedure is as follows. In a 2 L beaker containing 1 L of deionized water, 25.05 g (0.148 moles) of reagent grade silver nitrate is dissolved. Separately, in a 500 ml flask containing 250 ml of deionized water, 8.86 g (0.0369 moles) of reagent grade sodium sulfide nonahydrate ($Na_2S$ $9H_2O$) is dissolved. To this sodium sulfide solution is added 4.61 g (0.0369 mole) of sodium selenide. The solution is stirred to dissolve all solids.

The sulfide-selenide solution is transferred to a 250 ml separatory funnel suspended over the beaker containing the stirred silver nitrate solution. The sulfide-selenide solution is added dropwise to the stirred silver nitrate solution over a period of 30–60 minutes. After the addition is complete, the suspension is stirred at room temperature for an additional hour.

The precipitate is collected by filtration, washed with deionized water and methanol, and finally air dried.

The dry precipitate is stored in a brown glass bottle until use.

A precipitate containing Te rather than Se is made according to the procedure described above, substituting sodium telluride (6.41 g, 0.0369 moles) for sodium selenide.

Membrane materials containing Ag, S, and either As or Sb, believed to have the formula $Ag_3QS_3$, are made as follows. Reagent grade silver nitrate (25.48 g, or 0.150 moles) is dissolved, with stirring, in 1 L of deionized water in a 2 L beaker. Separately, in a 500 ml flask containing 250 ml of deionized water, 18.01 g (0.075 moles) of sodium sulfide nonahydrate is dissolved, with stirring. To the sulfide solution are added 8.49 g (0.025 moles) of antimony trisulfide. The solution is stirred until all solids have dissolved.

The antimony-sulfide solution is added dropwise to the silver nitrate solution and the product is collected, washed, and dried, as described above for silver sulfoselenide.

A precipitate containing As rather than Sb is made according to the above procedure, substituting arsenic trisulfide (6.15 g, 0.025 moles) for antimony trisulfide.

The above minerals or precipitates, alone or in combination with an additional membrane component, can then be made into membrane form, according to well-known methods, e.g. as described in Ross et al. U.S. Pat. No. 3,563,874. The membrane components are first each weighed out separately in the required proportions. In some instances there will be only one component, while in other instances at least one additional component, e.g. silver iodide, will also be present. The membrane components are combined and ground together using mortar and pestle to form a homogeneous mixture. The mixture is then cold-pressed into an electrode membrane, according to procedures well-known in the art. After cold-pressing, the membrane surface is highly polished, also according to well-known procedures. Polishing is important in obtaining maximum ion sensitivity.

The membranes of the invention are used in an electrochemical cell such as that shown diagrammatically in FIG. 1. Electrochemical cell 20 includes tube 22, which is open at both ends. The tube typically is formed of a liquid impervious, substantially rigid, electrically insulating material, such as epoxy (which is preferred), unplasticized polyvinylchloride, polytetrafluorethylene, glass or the like, substantially chemically inert to solutions being tested.

One end of tube 22 is sealed with membrane 24 of the invention. Membrane 24 can be quite thick, for example, ¼ inch, although thinner structures are preferred. Membrane 24 is preferably sealed across one end of tube 22 with an appropriate sealing compound such as an epoxy resin.

Disposed internally of tube 22 and in electrical and physical contact with the inner surface of the membrane 24 is charge transfer means providing a fixed concentration of silver either in metallic or ionic form. This means is shown as a reference electrolyte 30, for example, an aqueous saturated solution of suitable salts. Immersed in electrolyte 30 is internal referrence electrode 32, for example the well-known Ag-AgCl element. This combination of electrolyte 30 and reference electrode 32 provides means for electrically contacting the internal face (e.g., the surface of the membrane contacting the electrolyte) at a substantially stable or fixed potential.

The other open end of tube 22 is fitted with annular cap 34 having an aperture in which is sealed the usual coaxial cable 36, the central conductor of which is connected to internal reference electrode 32 and the peripheral conductor of which is intended to provide electrostatic shielding.

Figure 2:
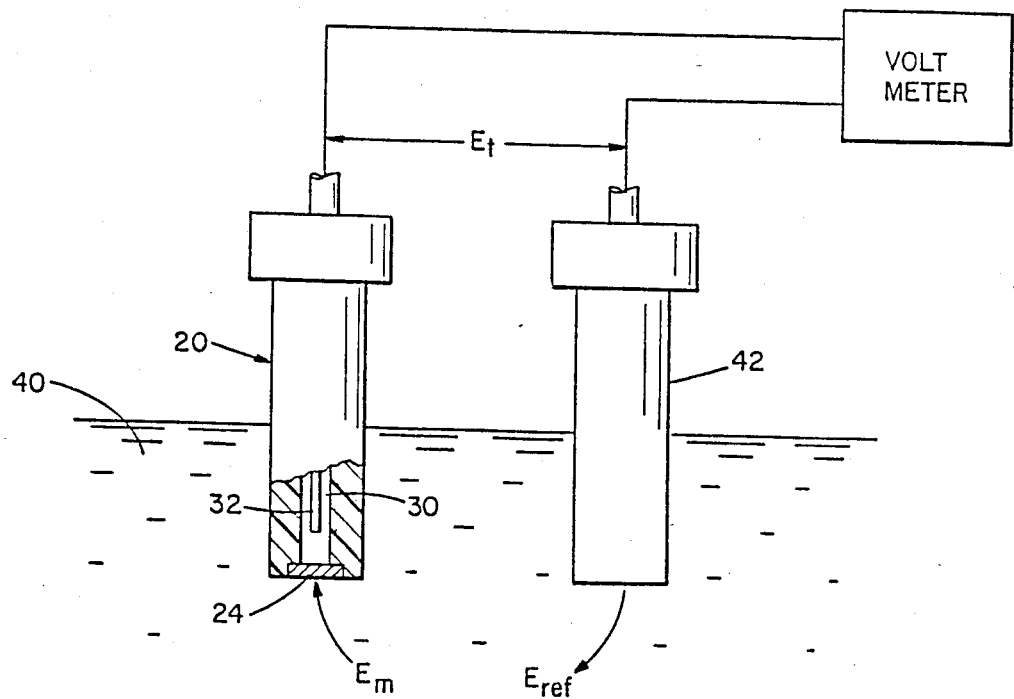
FIG. 2 is a diagrammatic representation of the cell of FIG. 1 used in conjunction with a reference cell.

As shown in FIG. 2, electrochemical cell in use is placed so that the outer surface of membrane 24 contacts solution 40 under test. A standard reference electrode 42 is also placed in contact with solution 40.

Reference electrode 42 is preferably a double junction reference electrode such as that sold by HNU Systems, Inc., Newton, MA under model number ISE 40-20-00. This reference electrode employs two solutions: an internal solution of 4M KCl, saturated with AgCl; and an external, silver-free solution of 1M NaNO$_3$. Both electrode 20 and reference electrode 42 are connected electrically to respective inputs of an electrometric device which is preferably the usual high-input impedance voltmeter.

In operation of the assembly of FIG. 2, a potential, $E_{ref}$ of substantially fixed value (assuming constant temperature conditions) develops between reference electrode 42 and solution 40 independently of the ion concentration in the latter. Another potential, $E_m$, will develop across membrane 24 between internal electrolyte 30 and solution 40. Because the potential, $E_{int}$ between reference electrode 32 and electrolyte 30 is also fixed, the total potential $E_t$ appearing between electrodes 42 and 20 will be the sum of $E_m$, $E_{ref}$, and $E_{int}$, and thus varies with $E_m$ only. $E_t$ can be readily measured on an electrometric device, thus indicating the presence and activity of the desired ions in solution 42.

Other embodiment of this invention will occur to those skilled in the art which are within the scope of the following claims.

What is claimed is:

1. An electrochemical cell comprising a reference electrode, an electrolyte, and an ion specific membrane, arranged to detect an ion in a solution, said ion specific membrane containing Ag, S, and Sb.

2. The electrochemical cell of claim 1 wherein said membrane contains a compound containing Ag and Sb.

3. An electrochemical cell comprising a reference electrode, an electrolyte, and an ion specific membrane, arranged to detect an ion in solution, said ion specific membrane comprising a ternary compound of Ag, S, and one of As, Sb, Se, or Te.

4. The electrochemical cell of claim 3 wherein said ternary compound has the formula $Ag_3QS_3$, wherein Q is As or Sb.

5. The electrochemical cell of claim 3 wherein said ternary compound has the formula $Ag_4SZ$, wherein Z is Se or Te.

6. The electrochemical cell of claim 3 wherein said ternary compound comprises between 10 and 90 mole % of said membrane.

7. The electrochemical cell of claim 1 or claim 3 wherein said membrane further comprises one of AgX, wherein X is a halogen; lead sulfide; cadmium sulfide; silver thiocyanate; silver cyanide; copper sulfide; or mercury sulfide.

8. An electrochemical cell comprising a reference electrode, an electrolyte, and an ion specific membrane, arranged to detect an ion in solution, said ion specific membrane containing Ag, S, and one of Sb, Te, As, or Se, said membrane being formed by a process comprising
 combining an aqueous solution of silver salt with an aqueous solution of a compound containing S and one of Se, Sb, Te, or As to form a precipitate containing Ag, S, and one of Se, Sb, Te, or As, and
 subjecting said precipitate to elevated pressure at a temperature lower than 100° C. to form said membrane.

9. A method of making an ion specific membrane for use in an electrochemical cell comprising
 combining an aqueous solution of a silver salt with an aqueous solution of a compound containing s and one of Se, Sb, Te, or As to form a precipitate containing Ag, S, and one of Se, Sb, Te, or As, and
 subjecting said precipitate to elevated pressure at a temperature lower than 100° C. to form said membrane.

10. The method of claim 9 wherein, prior to subjecting said precipitate to pressure, said precipitate is combined with one of AgX, wherein X is a halogen; lead sulfide; cadmium sulfide; silver thiocyanate; silver cyanide; copper sulfide; or mercury sulfide.

* * * * *